(12) United States Patent
Squilla et al.

(10) Patent No.: US 7,139,016 B2
(45) Date of Patent: Nov. 21, 2006

(54) INTRA-ORAL CAMERA SYSTEM WITH CHAIR-MOUNTED DISPLAY

(75) Inventors: John R. Squilla, Rochester, NY (US);
John T. Boland, Fairport, NY (US);
John P. Spoonhower, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 481 days.

(21) Appl. No.: 10/727,960

(22) Filed: Dec. 4, 2003

(65) Prior Publication Data

US 2004/0114034 A1 Jun. 17, 2004

Related U.S. Application Data

(63) Continuation-in-part of application No. 10/238,174, filed on Sep. 10, 2002, which is a continuation-in-part of application No. 09/796,239, filed on Feb. 28, 2001.

(51) Int. Cl.
*H04N 7/18* (2006.01)
(52) U.S. Cl. .......................................... 348/66; 348/65
(58) Field of Classification Search ............ 348/65–76
See application file for complete search history.

(56) References Cited

U.S. PATENT DOCUMENTS 5,527,261 A * 6/1996 Monroe et al. ............. 600/109
6,132,211 A 10/2000 Peithman ..................... 433/29
2002/0067407 A1* 6/2002 Cooper ......................... 348/66
2002/0118279 A1 8/2002 Spoonhower et al. ......... 348/66
2003/0016284 A1 1/2003 Squilla et al. ................ 348/66
2004/0007907 A1* 1/2004 DiRe ....................... 297/217.3

* cited by examiner

*Primary Examiner*—Andy Rao
(74) *Attorney, Agent, or Firm*—Nelson Adrian Blish

(57) ABSTRACT

A portable intra-oral capture and display system, designed for use by a dental practitioner in connection with a patient seated in a dental chair, includes: a handpiece elongated for insertion into an oral cavity of the patient, where the handpiece includes a light emitter on a distal end thereof for illuminating an object in the cavity and an image sensor for capturing an image of the object and generating an image signal therefrom; a monitor interconnected with the handpiece, where the monitor contains electronics for processing the image for display and a display element for displaying the image, where the interconnection between the monitor and the handpiece includes an electrical connection for communicating the image signal from the image sensor in the camera to the electronics in the monitor; and a receptacle on the dental chair for receiving the monitor, wherein the receptacle conforms to the monitor such that the monitor may be withdrawn from the receptacle in order to allow the display element to be seen by the dental practitioner or the patient.

9 Claims, 14 Drawing Sheets

INTRA-ORAL CAMERA SYSTEM WITH CHAIR-MOUNTED DISPLAY

CROSS REFERENCE TO RELATED APPLICATIONS

This patent application is a continuation-in-part of commonly-assigned U.S. patent application Ser. No. 10/238,174, which was filed on Sep. 10, 2002, which is a continuation-in-part of commonly-assigned U.S. patent application Ser. No. 09/796,239, which was filed on Feb. 28, 2001.

FIELD OF THE INVENTION

The present invention relates to intra-oral imaging systems for dental applications, and particularly to an intra-oral camera system that is used by a dental practitioner to display images of objects in the mouth.

BACKGROUND OF THE INVENTION

Electronic handheld cameras configured with intra-oral imaging optics are used for capturing images of the inside of a patient's mouth. The camera typically has an elongated body that contains an image sensor and optics. The optics and sensor are designed for capturing images of the inside of the mouth when the distal or viewing end of the camera is inserted into the patient's mouth. Wires carrying electronic signals typically connect the image sensor to the proximal end of the camera where a communication interface is provided to an image processing system or display monitor that allows manipulation and display of the images. By viewing the displayed images, a diagnosis can be made and appropriate treatment prescribed.

For illuminating the inside of the mouth, a fiber optic cable typically is used to transmit light to the viewing end of the camera. The light is generated by a high intensity light source such as a lamp or bulb typically held in a light box. In a typical embodiment, such as shown in U.S. Pat. No. 6,132,211, the fiber optic cable terminates in a connector that plugs into a power source housing that also includes the light source. Preferably, the housing for the power supply and the light source is supported on a countertop or on a post in the dental operatory room. In other words, the housing is basically immovable and portability is provided by having the portable handpiece removable from the housing. According to the '211 patent, this design is chosen so that any number of operatories having a power source base and display may be serviced by a single handpiece system.

In a typical installation, the housing containing the power supply and the light box includes a communications interface to an external image processing system or display monitor. This leads to various placements of the processor and monitor. For instance, in the Reveal® Imaging Platform sold by Welch Allyn® the monitor is mounted on top of the housing, which makes the whole assembly virtually unmovable. Consequently, similar to what was described above in connection with the '211 patent, in the Reveal® Imaging Platform the handpiece is plugged into a receptacle on the housing.

The use of intra-oral cameras among dental practitioners is well known. Besides their use in the diagnosis of dental and oral disease, they are used as well in providing a visual record of the condition of the patient. It is frequently the case that a dentist, orthodontist, or the like, may have multiple operatories where the use of such a camera is desirable. Current camera systems require either the use of an attached computer system and video monitor, or a separate monitor for the display of images. Thus the practitioner is required to either purchase multiple camera systems or display capabilities for each operatory, as such display systems are rather large and bulky.

In many cases, a dentist desires to produce images of the interior of a patient's mouth in order to provide both a diagnosis of dental and oral disease as well as to provide a visual record of the condition of the patient. This process becomes cumbersome, costly, and inconvenient, as current camera systems are not designed for portability. What is needed is a truly portable camera system that would incorporate an integral display and provide advantages over the current state-of-the-art. Because of size and portability issues, were such a camera and display system to become available, it would be desirable to maximize ease of use despite the small size and minimize the possibility of contamination due to dentist and patient interaction with the system.

SUMMARY OF THE INVENTION

The present invention is directed to overcoming one or more of the problems set forth above. Briefly summarized, according to one aspect of the present invention, the invention resides in a portable intra-oral capture and display system for use by a dental practitioner in connection with a patient seated in a dental chair. The system includes: a handpiece elongated for insertion into an oral cavity of the patient, said handpiece including a light emitter on a distal end thereof for illuminating an object in the cavity and an image sensor for capturing an image of the object and generating an image signal therefrom; a monitor interconnected with the handpiece, said monitor containing electronics for processing the image for display, and a display element for displaying the image, where the interconnection between the monitor and the handpiece includes an electrical connection for communicating the image signal from the image sensor in the camera to the electronics in the monitor; and a receptacle on the dental chair for receiving the monitor, wherein the receptacle conforms to the monitor such that the monitor may be withdrawn from the receptacle in order to allow the display element to be seen by the dental practitioner or the patient.

The advantage of the present invention lies in the integration of the display into a dental chair. This integration enables the practitioner to easily view and act upon the the results of image recording in close proximity to the capture location by interaction with the system, and conveniently display the captured image(s) either for the practitioner's or patient's benefit.

These and other aspects, objects, features and advantages of the present invention will be more clearly understood and appreciated from a review of the following detailed description of the preferred embodiments and appended claims, and by reference to the accompanying drawings.

DESCRIPTION OF THE PREFERRED EMBODIMENTS

Because intra-oral cameras employing electronic sensors are well known, the present description will be directed in particular to elements forming part of, or cooperating more directly with, apparatus in accordance with the present invention. Elements not specifically shown or described herein may be selected from those known in the art. Certain aspects of the embodiments to be described may be provided in software. Given the system as shown and described according to the invention in the following materials, software not specifically shown, described or suggested herein that is useful for implementation of the invention is conventional and within the ordinary skill in such arts.

Figure 1:
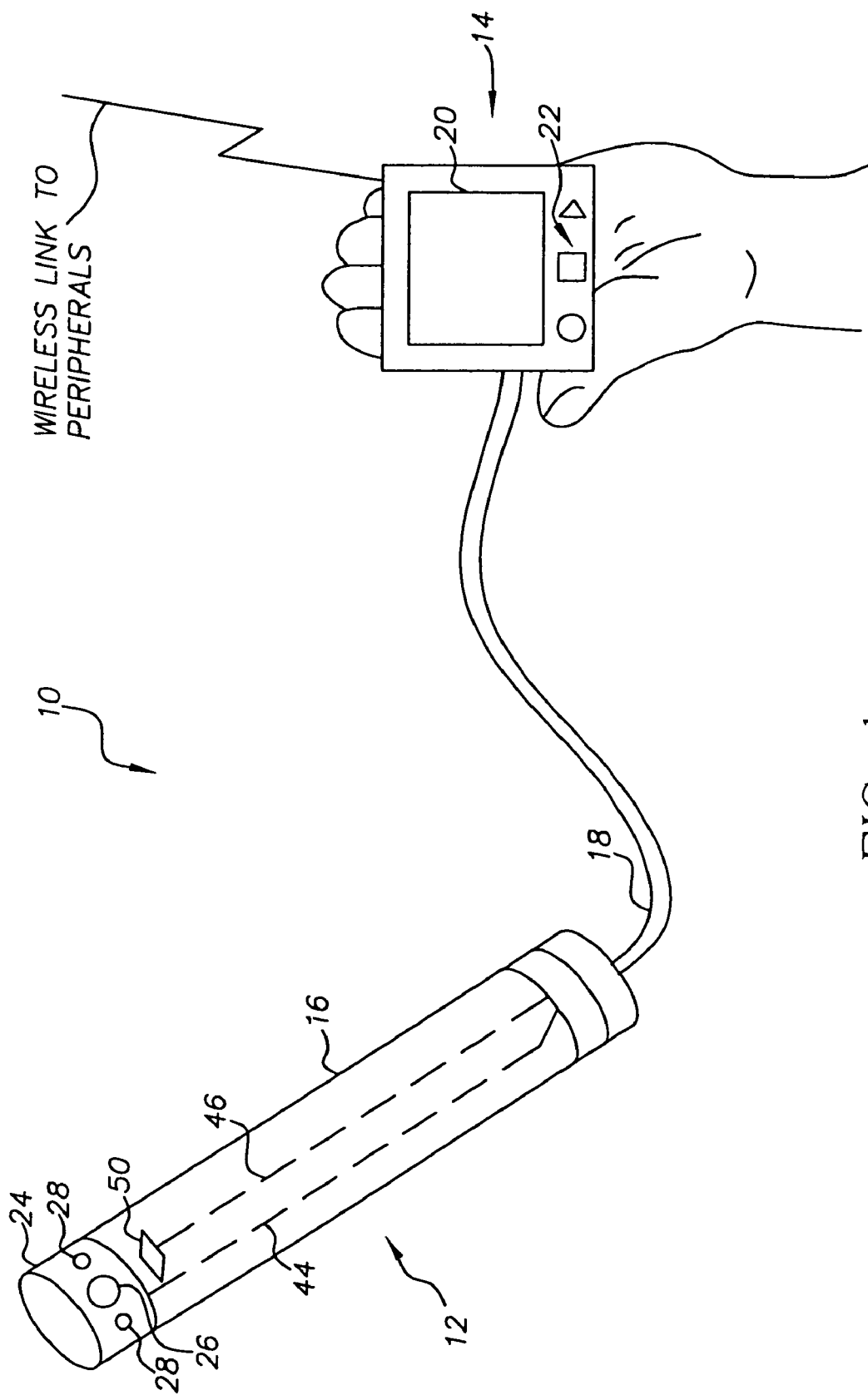
FIG. 1 shows an intra-oral camera and display system according to the invention.

Referring first to FIG. 1, an intra-oral dental camera system 10 includes a portable dental camera 12 and a power source, illumination source and a display unit integrally located in a portable enclosure (hereinafter referred to as the integral base 14) tethered to the camera 12. The camera 12 and the integral base 14 thus constitute, in the terms of this invention, an intra-oral camera with integral display. The dental camera 12 includes a handpiece 16 and a cable 18 connecting the dental camera 12 to the integral base 14. As shown for illustrative purposes in FIG. 1, the integral base 14 can be easily cradled in a hand, and includes a display monitor 20 that can be easily hand positioned relative to the dentist's and/or patient's line of sight. A set of user controls 22 are provided on the integral base 14 that can be easily hand-navigated for controlling the illumination and the images displayed on the monitor, as well as communicating with peripheral devices. The handpiece 16 supports a removable lens unit 24 that includes a lens 26 and light emitting apertures 28. The handpiece 16 is generally elongated and cylindrical with a central axis. The lens 26 is positioned to receive light impinging on the handpiece in a direction substantially perpendicular and normal to the central axis of the handpiece.

Figure 2:
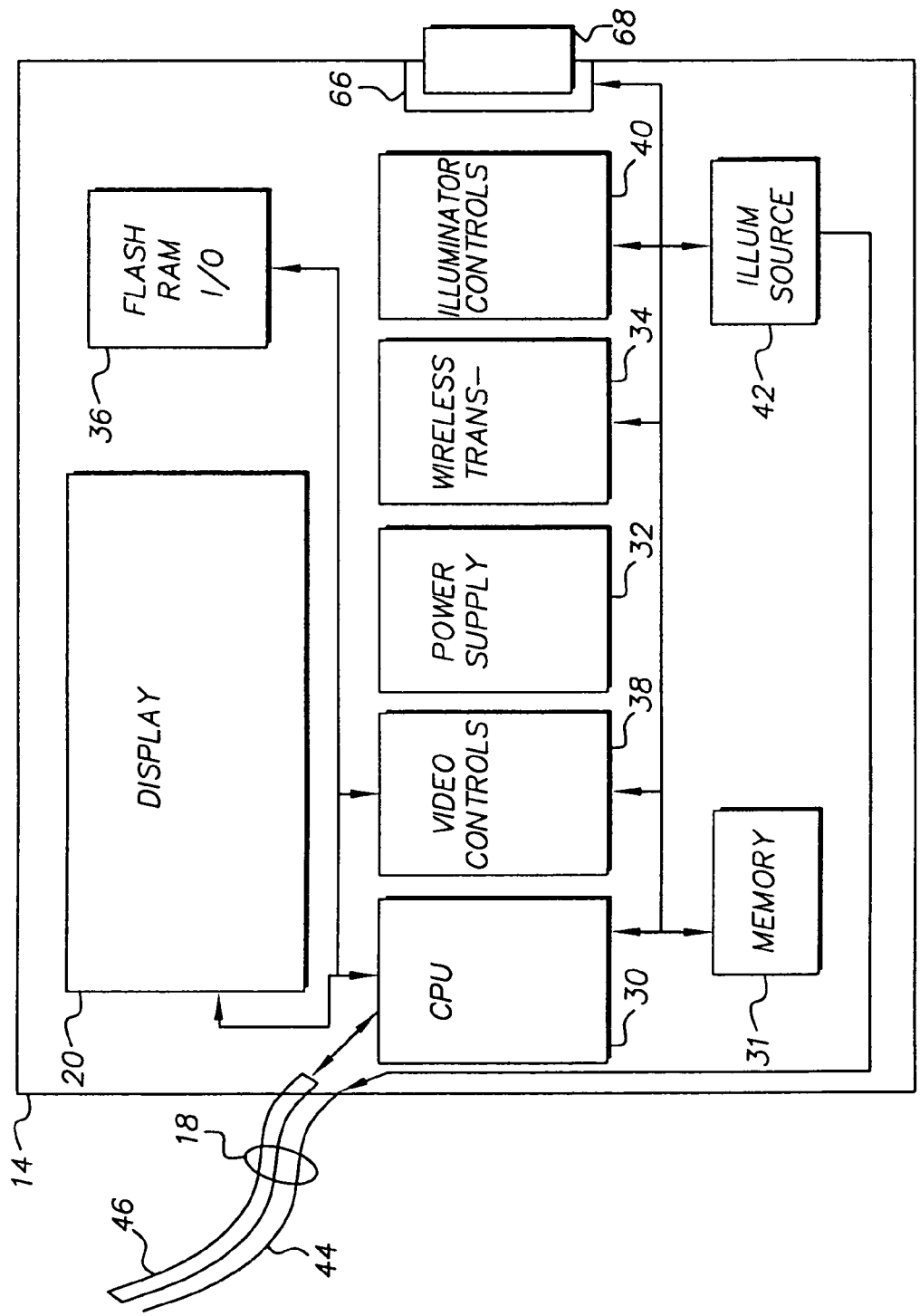
FIG. 2 shows a block diagram of the electronics in the integral base.

Referring to FIG. 2, the integral base 14 further includes a central processing unit (CPU) 30, a CPU memory 31, a power supply 32, a wireless transceiver 34, and flash memory (RAM) 36. The user controls 22 interface with a video control unit 38 and an illuminator control unit 40. The illuminator control unit 40 connects with an illumination source 42, which provides illumination to the handpiece 16 through a fiber optic 44 that is part of the cable 18. The illumination source may take a variety of forms known to those of skill in this art, such as a halogen arc lamp lighting system or a tungsten/halogen lamp. The power supply 32 is connected by a power cable (not shown) to a power source, such as a wall socket. The image signal communication between the handpiece 16 and the CPU 30 is maintained through an electrical connection 46, which is also in the cable 18. While not shown in detail, the handpiece 16 also supports a connection of the fiber optic 44 with the light emitting apertures 28 and a connection of the electrical conductor 46 to an image sensor 50, such as a conventional charge coupled device (CCD). The image sensor 50 is arranged in a conventional optical path, with mirrors and other optical components as might be necessary, such that the lens 26 can form an image of an intra-oral object on the image sensor 50.

It should be noted that portability is facilitated by incorporating into the dental camera system 10 both a high quality image display 20 along with means to transfer image data to a physically separate and distinct data storage associated with an image printing capability. The high quality image display may be provided by a number of well-known technologies; for example, it is well-known in the art of hand-held televisions (e.g., the Casio EV660 Color Active Matrix Handheld TV) to use a small (e.g., 3 inch) screen with thin-film transistor active matrix (TFT) technology. The means to accommodate a transfer of image data may include (a) wireless RF or microwave transceiver technology, (b) wireless infra-red transmission technology, and/or (c) removable memory technology embodied in physically small elements, such as flash RAM cards or small hard drives, that are easily removed from the camera part of the system and subsequently plugged into either the image data storage or printer parts of the system.

Figure 3:
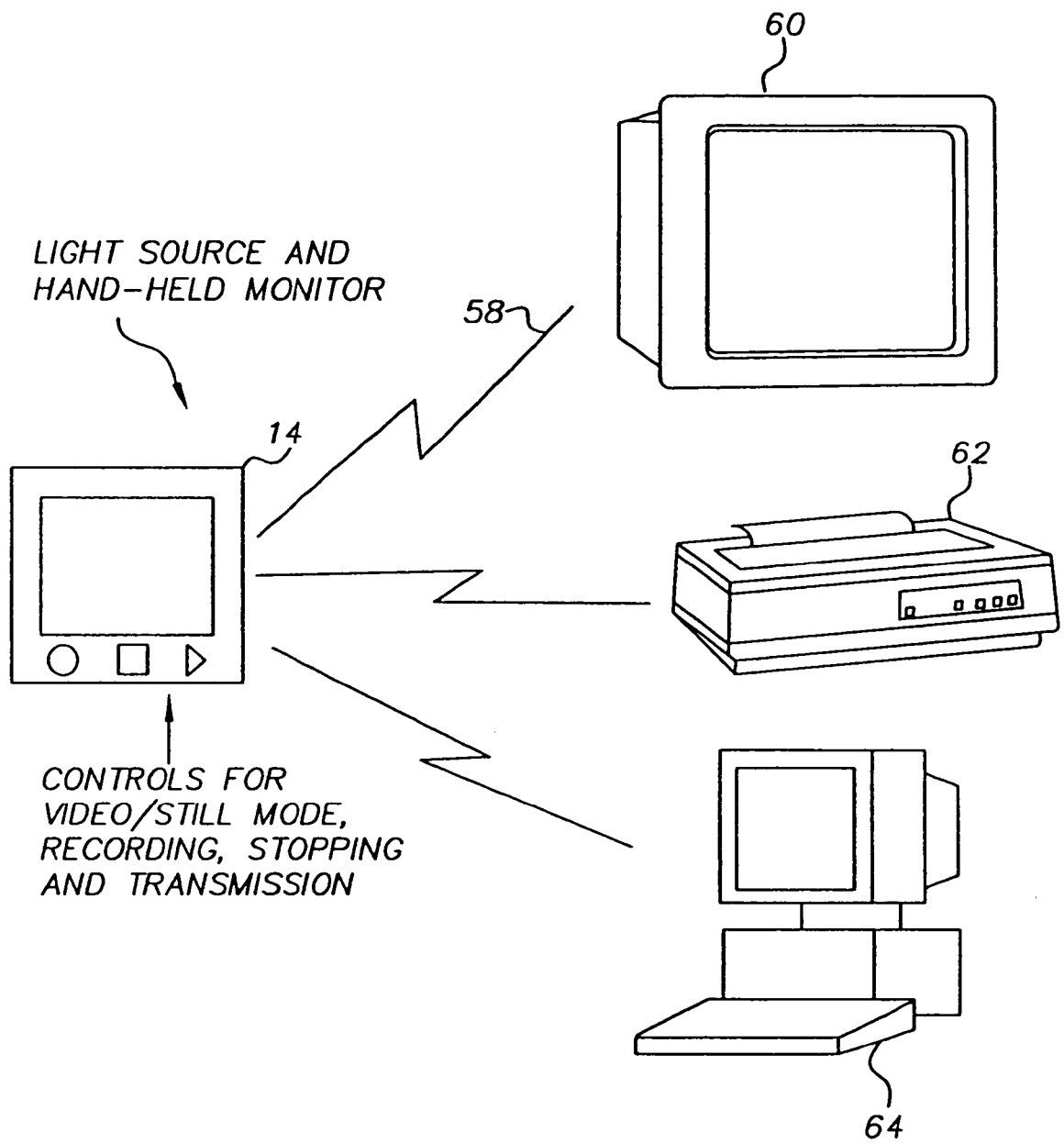
FIG. 3 shows the integral base for the light source and hand held monitor of the system shown in FIG. 1, particularly as it would be used for communication to a group of peripherals, including communication of color coordinates for an intra-oral object to an offsite dental facility for the fabrication of a prosthetic.

Accordingly, the dental camera system 10 can, through the transceiver 34 in its integral base 14, initiate communication via wireless links 58 with a variety of peripheral units as shown in FIG. 3. Each of these units would have its own data storage for receiving the transmitted images. Without intending to be exhaustive as to type of peripheral unit that may be accessed, such peripheral units include a larger monitor or television receiver 60, a printer 62, and a computer system 64, such as any conventional desktop PC, where the images may be stored. With this arrangement, a dental practitioner may view an image on the integral base 14 and immediately initiate its transfer to any one of the peripheral units 60, 62 or 64 by means of the user controls 22. The incorporation of the transceiver 34 and the display monitor 20 into the dental camera system 10 further enables the practitioner to view the results of an image recording, and conveniently display the captured image(s) either for the practitioner's or patient's benefit. For this purpose, the transceiver 34 would receive images from a storage peripheral, such as the computer system 64, and display the stored images on the display monitor 20. Importantly, such viewing occurs without the requirement of producing a physical print of the image.

Just as importantly, with this arrangement the practitioner can separate the movable, but clumsy and sometimes bulky, printing and processing operation from the dental operatory, and devote a particular room to these peripherals. Moreover, incorporation of the display as a tethered adjunct to the camera system removes the requirement on the dentist to move a large bulky system (a video monitor and/or attached computer) from one operating room to the next. Alternatively, the requirement that the dentist purchase multiple such systems for multiple operatories is eliminated.

In a preferred embodiment, the image sensor 50 provides an image signal that the CPU 30 processes (as a video signal) for display on the display monitor 20. The video control unit 38 interacts through the CPU 30 and the user controls 22 to provide functionality for several modes, including a video/still mode, a mode for initiating a recording of a still or video sequence, a mode for stopping the imagery at any point (freeze-frame), a mode for initiating transmission to any of the peripherals shown in FIG. 3 and a mode for initiating retrieval of a stored image from an external memory, e.g., from the computer system 64. In the latter two modes, the images are transmitted and/or received via an antenna or light beam emitter (not shown) to/from any of the peripherals 60, 62 or 64. Alternatively, the images may be stored in a removable memory and the removable memory is then transported to the peripheral units. For instance, the integral base 14 may also include a receptacle 66 for a physically small RAM card 68, which may be easily removed from the integral base 14 and subsequently plugged into a corresponding receptacle (not shown) in any one of the peripheral units 60, 62 and 64.

Figure 4:
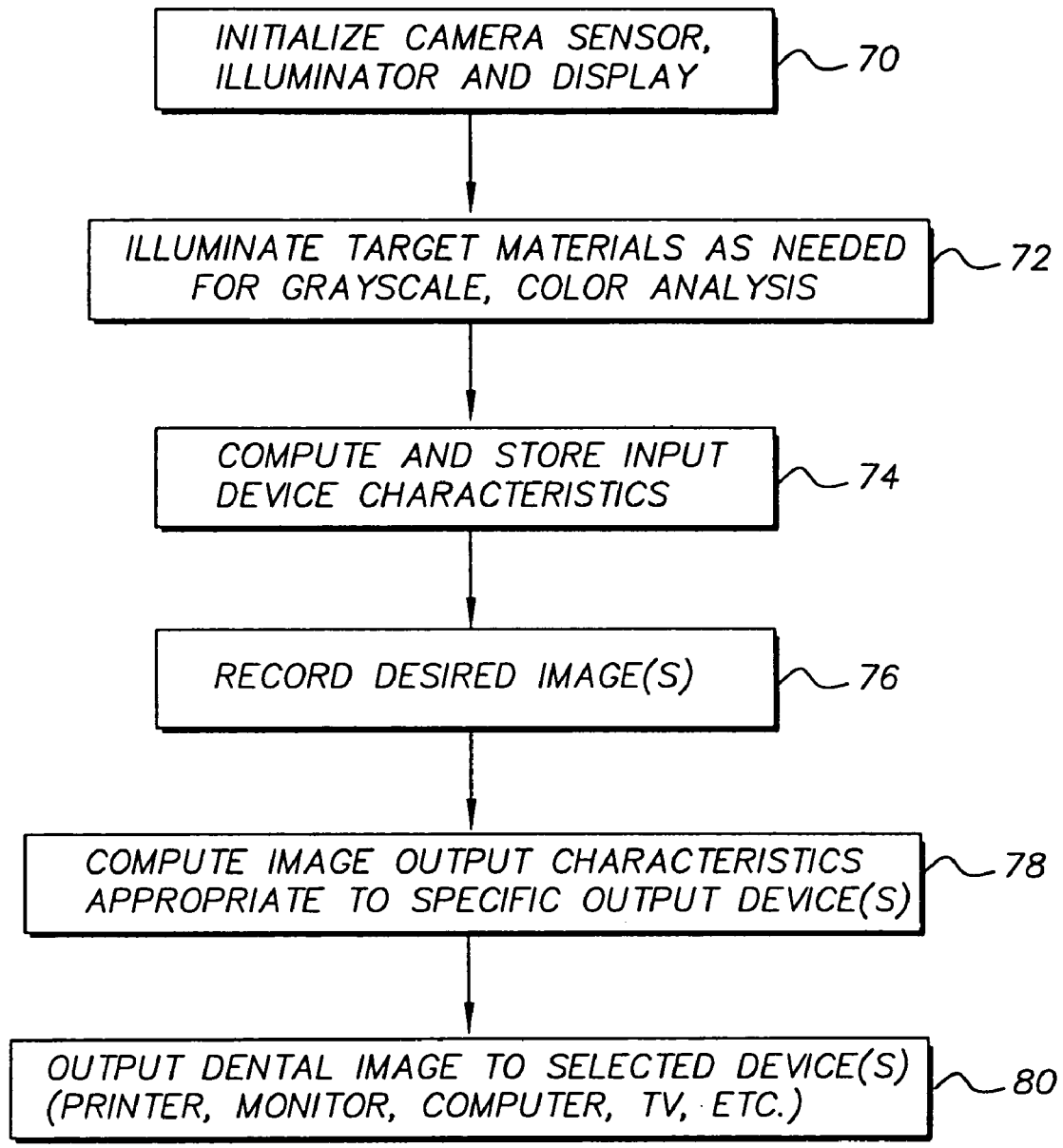
FIG. 4 shows a flow chart for a process for correcting the color of the system shown in FIG. 1.

In order to adjust the colorimetry of the dental camera system 10 to match the color of intra-oral objects, e.g., to match a natural tooth color, it is desirable to provide an optimum color calibration for an intra-oral camera application. FIG. 4 shows the process for correcting the color of a system designed for the collection of intra-oral images. It is desirable to have a broadband match (broadband spectrum) because of the need to match teeth under a variety of illumination conditions. The camera is first initialized in a stage 70 to clear previous color correction factors from the CPU memory 31. These can be in the form of look up table elements, matrix elements, and the like. As is well-known in the color management arts, these digital data are used in a mathematical transformation process to modify the color characteristics of components of the system to allow for a true color rendition to occur throughout the system. The illuminator is allowed to stabilize for a period of time so that the spectral output of the illumination source 42 remains the same for a period of time that allows multiple images to be captured, without the need for adjustment of the illuminator color temperature (or spectral output characteristics). The display monitor 20 may also require a period of stabilization before use.

In stage 72, target materials are illuminated with the illumination source 42 so as to characterize the image recording response. Such target materials can include, but are not limited to, color matching charts for the fabrication of color-matched prostheses. For example, the target materials would include the white(s) that dental practitioners use to match teeth for prosthetic purposes, such as the fabrication of a crown. (Note that calibration would ordinarily not be done with the intra-oral camera in a patient's mouth; the camera would typically be hooked up to the computer 64 for this calibration process.) Calibration of the system includes measurements of such targets to establish the characteristic input color response for the intra-oral camera system. The characteristic is stored digitally in stage 74 in the CPU memory 31 and used to transform the unknown color of the teeth (which are imaged in a separate image recording event or events resulting from stage 76) to a color representation within the system that can be used to produce a "true-color" output. The calibration of each output device is also performed and stored in stage 78 in the respective memories (not shown) of each output device. Then, the dental image is output to a selected output device(s) in stage 80, e.g., to the display monitor 20 or any of the output devices 60, 62 and 64 shown in FIG. 3. In this manner, the system can correct for color imbalance in any of the components in the system and render color corrected output regardless of the output channel.

In addition to the many output channels considered in FIG. 3, and the transmission of a color corrected image to an output device, transmission of data describing the color of a tooth or teeth is valuable. Using a color corrected system such as described above would enable a practitioner to accurately determine the color of a patient's teeth with the purpose of replicating the color in a prosthesis. Thus the practitioner could "shade match" a crown or other prosthetic device to the tooth to be replaced or other teeth proximate to the replaced tooth. Color matching calculations can be performed in CPU memory 31 and the results of such a calculation, the color coordinates of the tooth in question, can be transmitted over a computer network, e.g. the Internet, connected to the computer system 64 shown in FIG. 3, or via other means, e.g., disk or tape, to a lab technician in an offsite location, such as a dental laboratory facility (not shown), where an appropriate prosthetic device would be fabricated. (Alternatively, under certain situations the prosthetic device may be fabricated in the dental operatory or elsewhere in the dentist's own facility.)

Figure 5:
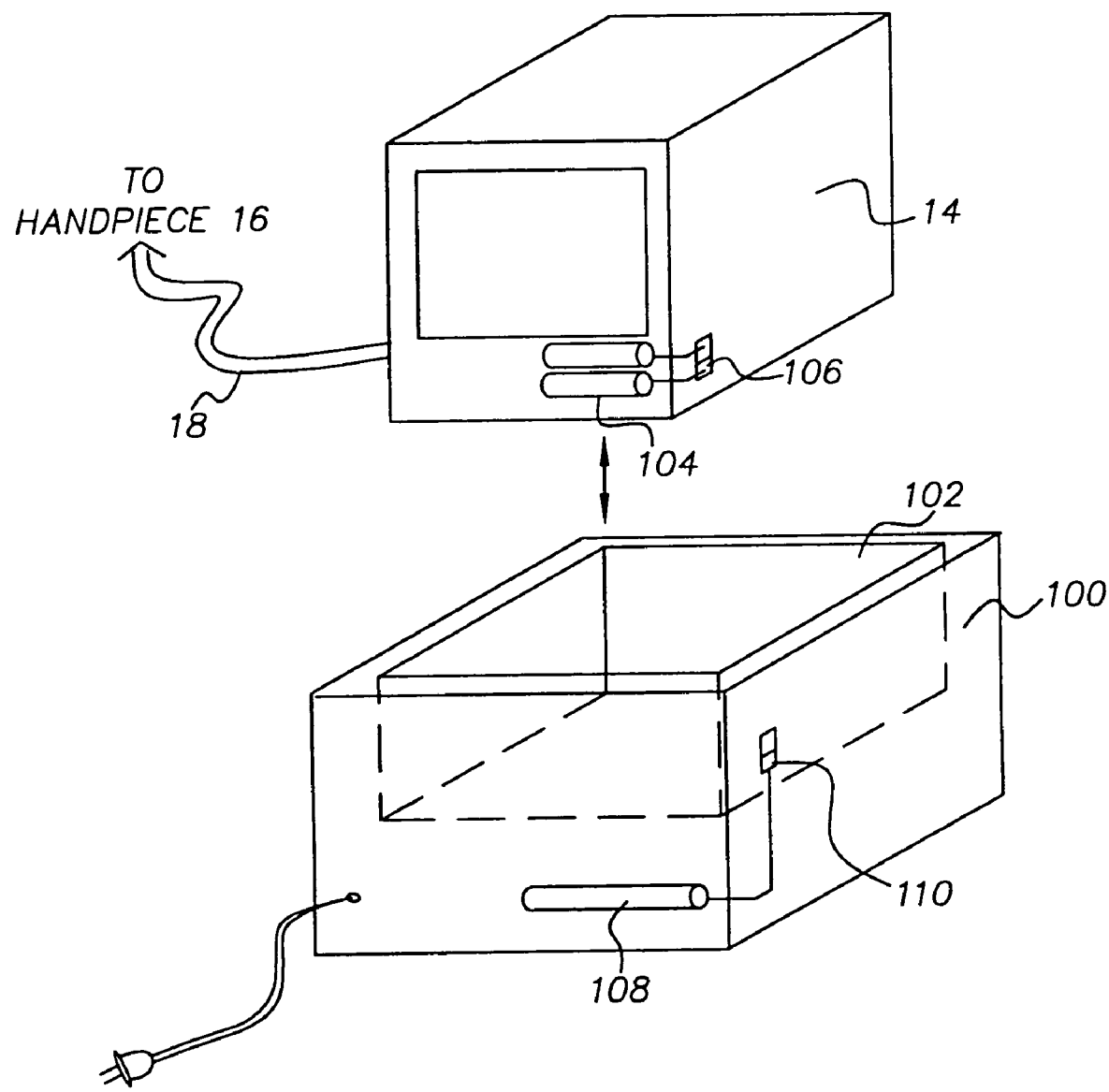
FIG. 5 shows a second embodiment of an intra-oral camera and display system according to the invention.

In a second embodiment of the intra-oral camera and display system shown in FIG. 5, the system includes a docking unit 100 with a recessed area 102 for mating with the integral base 14. The power supply 32 in the integral base 14 includes rechargeable batteries 104 connected to externally accessible charging electrodes 106. The docking unit 100 is provided with a battery charger 108 connected to externally accessible charging electrodes 110. When the integral base 14 is inserted into the recessed area 102 on the docking unit 100, the electrodes 106 and 110 are electrically connected and the batteries 104 are recharged.

Figure 6:
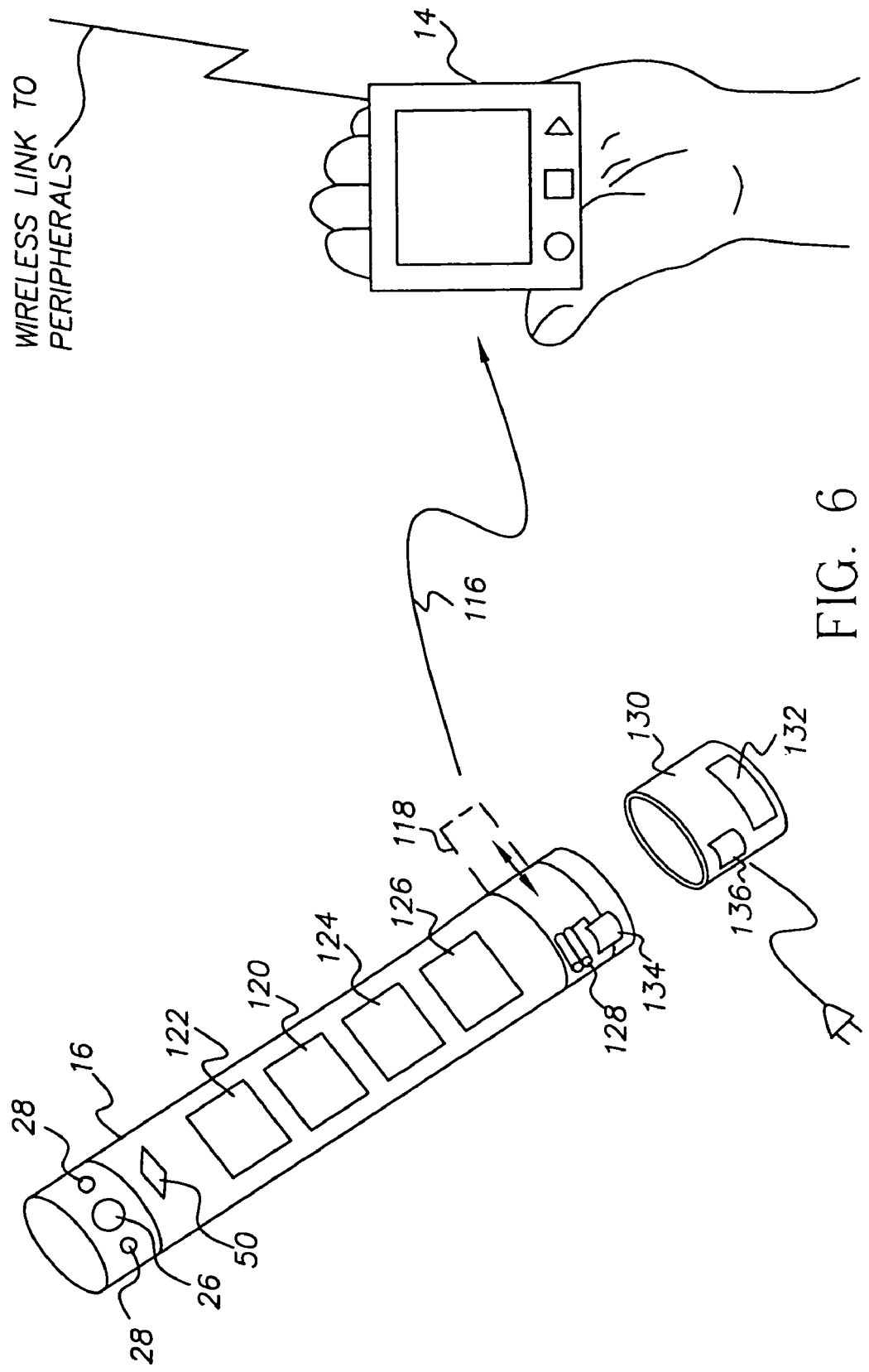
FIG. 6 shows a third embodiment of an intra-oral camera and display system according to the invention.

In a third embodiment of the intra-oral camera and display system shown in FIG. 6, the handpiece 16 of the system includes electronics and an interface for communicating with the integral base 14 across a wireless transmission linkage 116 or by means of a removable memory 118. More specifically, the handpiece 16 includes its own light source 120, processor 122, transceiver 124 and power supply 126. In addition, the power supply 126 may include rechargeable batteries 128, and the intra-oral camera and display system can further include a docking unit 130 with a battery charger 132. Both the handpiece 16 and the docking unit include mating electrodes 134 and 136 such that when the handpiece 16 is inserted into the docking unit 130, the electrodes 134 and 136 are electrically connected and the batteries 128 are recharged. In addition, as shown in FIG. 5, the integral base may have its own docking unit; moreover, the two docking units could be combined in one component.

Figure 7A:
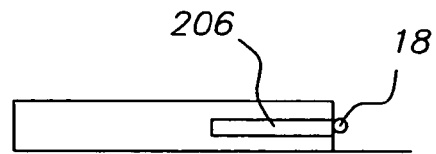
FIGS. 7A–7D show a first embodiment of a contamination control device for use with the display system shown in FIG. 1.
Figure 7B:
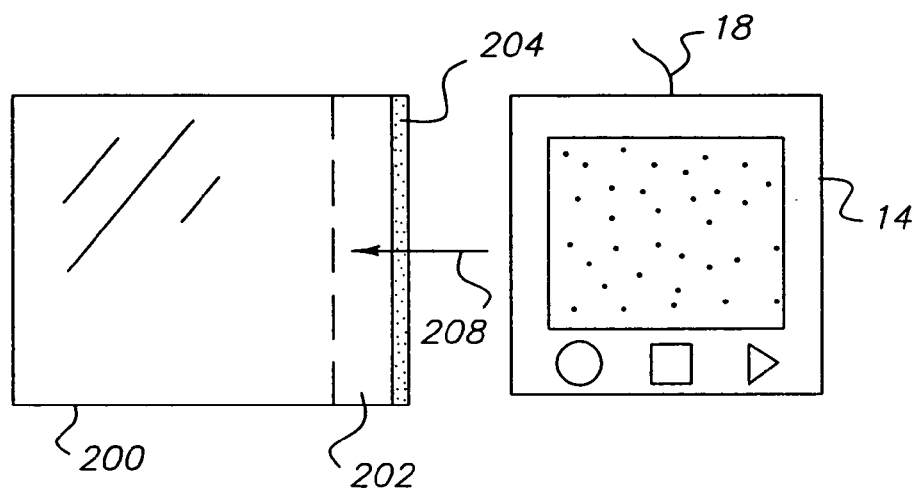
Figure 7C:
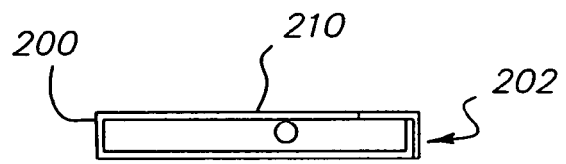
Figure 7D:
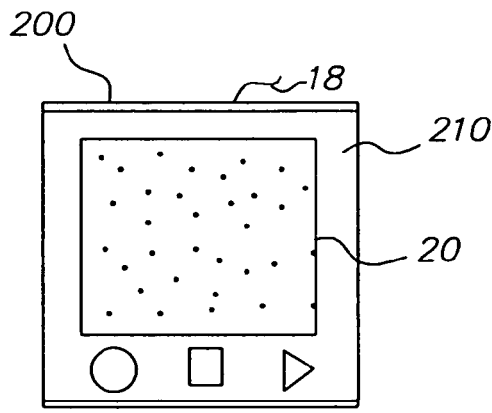

Because of the likelihood of contamination due to contagious afflictions that can be passed on to patients and staff when the same device is used with more than one patient, a contamination control device may be added to the intra-oral capture and display system. In an embodiment of the invention shown in FIGS. 7A–7D, the contamination control device is a clear sleeve or pouch 200 having a flap 202 lined with an adhesive 204. One side of the pouch 200 has a slot 206, as shown in a top view in FIG. 7A, which provides clearance for the cable 18 (of course, if the connection with the camera is a wireless connection, then the slot 206 is unnecessary and may be omitted). As shown by the arrow 208 in FIG. 7B, the integral base 14 slides into the pouch 200 and the flap 202, as shown in a top view in FIG. 7C, is closed; the pouch is than used with a single patient and then disposed after the patient's visit. In a front view, as shown in FIG. 7D, the display monitor 20 is visible through the transparent front panel 210 of the pouch 200.

Figure 8A:
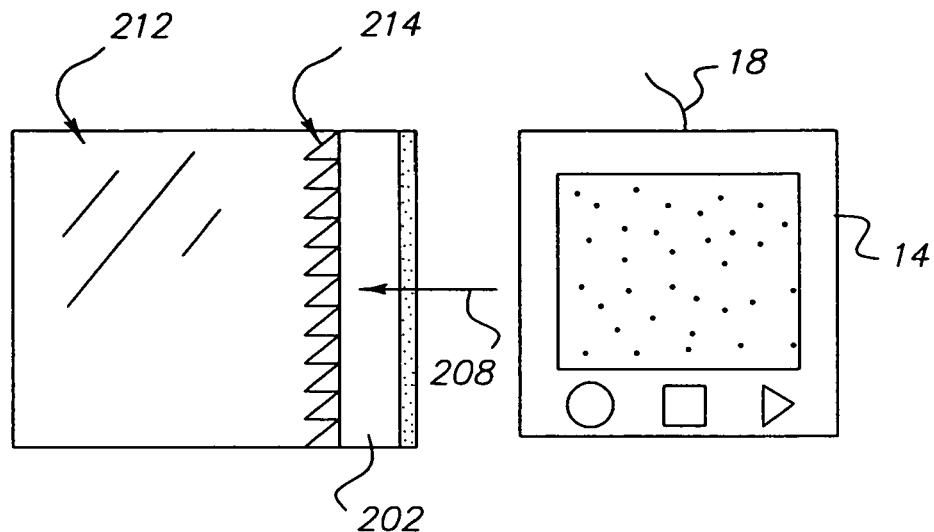
FIGS. 8A–8C show a second embodiment of a contamination control device for use with the display system shown in FIG. 1.
Figure 8B:
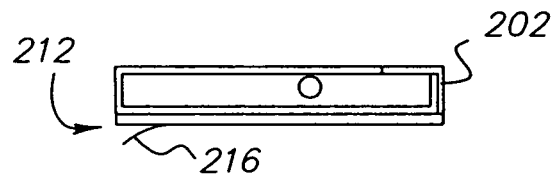
Figure 8C:
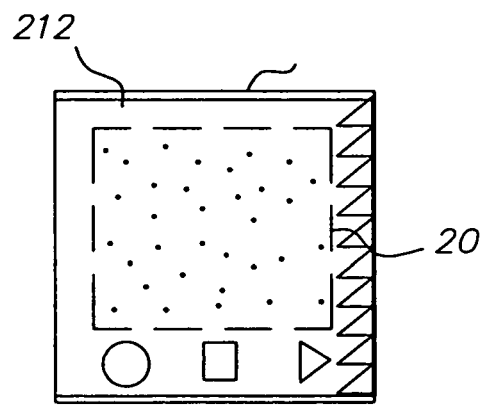

FIGS. 8A–8C show an alternate embodiment of the pouch 200 including multiple clear layers 212 attached to the front of the pouch 200 by a plurality of tear off tabs 214. As shown by the arrow 208 in FIG. 8A, the integral base 14 slides into the pouch 200 and the flap 202, as shown in a top view in FIG. 8B, is closed. In a front view, as shown in FIG. 8C, the display monitor 20 is visible through the transparent multiple clear layers 212 on the front of the pouch 200. In use, as shown in the top view in FIG. 8B, the top layer 216 of the multiple clear layers 212 can be peeled off at the tear off tabs 214 and thrown away, revealing a clean, sterile layer for the next patient.

Figure 9:
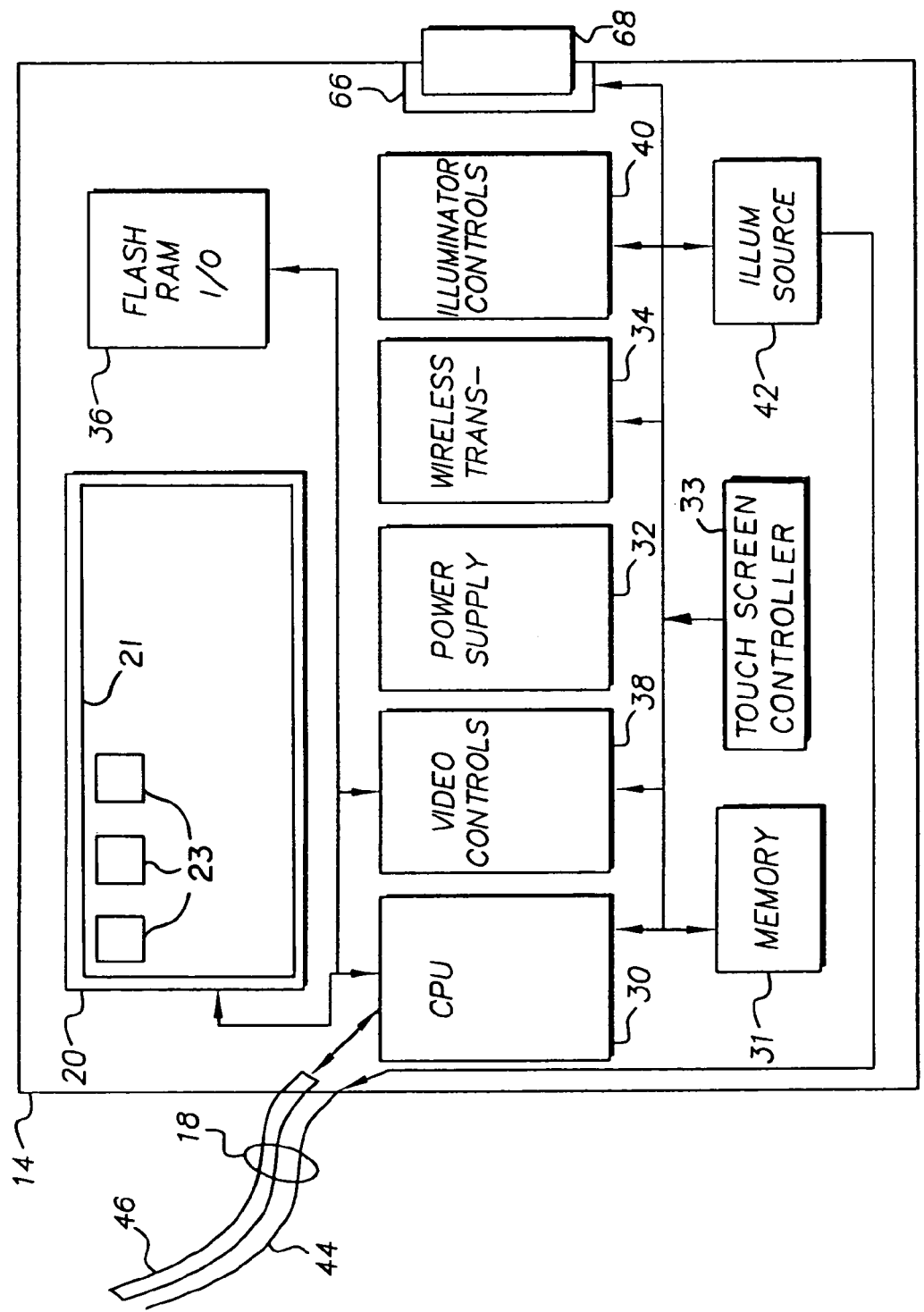
FIG. 9 shows a block diagram of the electronics in the integral base according to a further embodiment including a touch screen capability.
Figure 10:
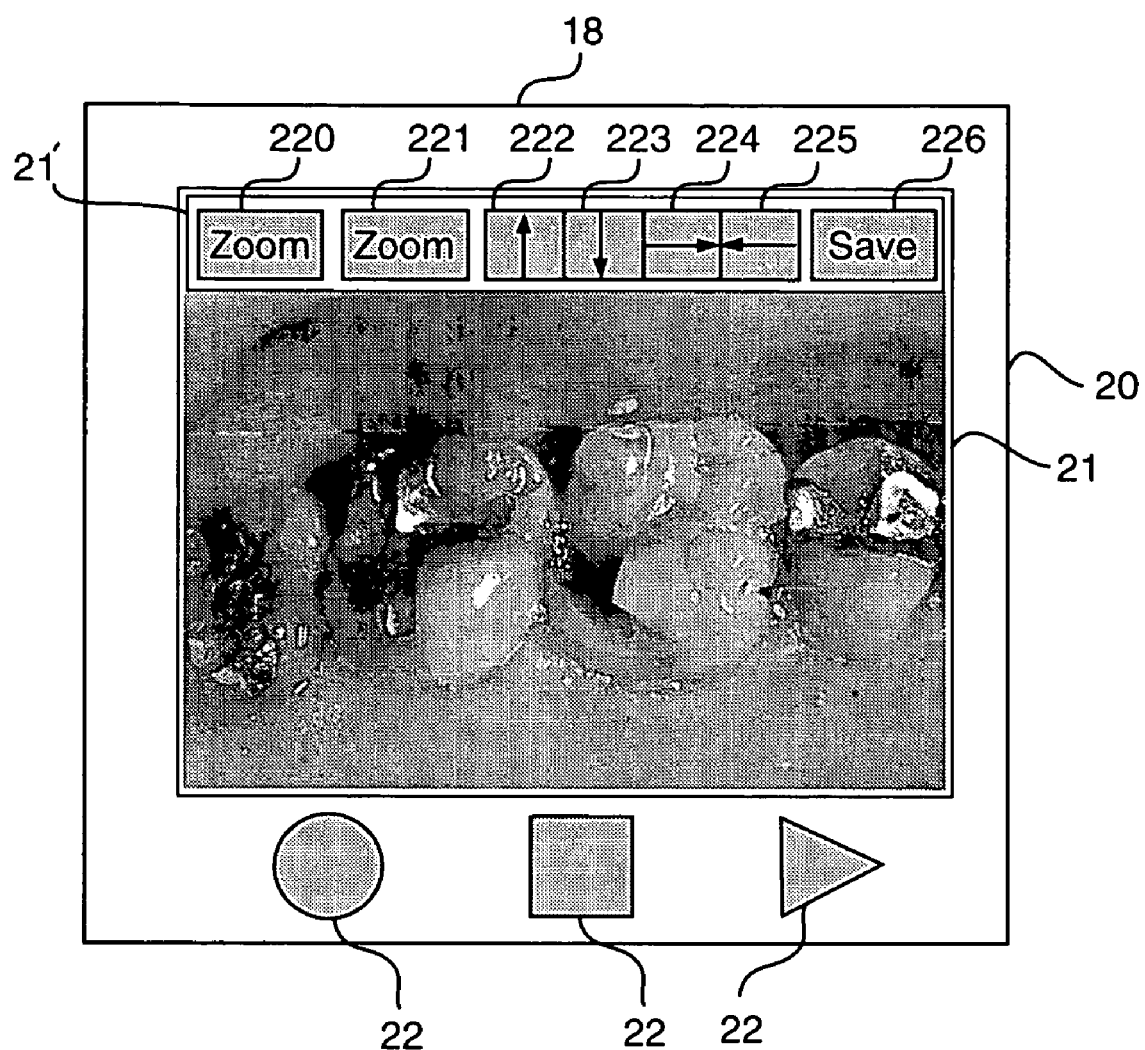
FIG. 10 shows a touch screen display for use with the intra-oral camera and display system shown in FIG. 1.

FIG. 9 shows the block diagram of the electronics in an integral base that includes a touch screen capability according to the invention. Most of the electronics in FIG. 9 is the same as shown in FIG. 2, and common electronic components sharing the same reference characters as in FIG. 2 will not be further described unless they relate in particular to the touch screen capability. A touch screen is a type of display screen that has a clear touch sensitive transparent panel 21 covering the screen of the monitor 20. Instead of using a pointing device such as a mouse or a light pen, a finger may be used to point directly at objects (touch screen controls 23) on the screen of the display monitor 20. The touch sensitive panel 21 may be sized to fit over substantially the entire display screen 20 or it may fit over a limited area 21' (see FIG. 10) of the display screen where it is desirable to locate a set of touch sensitive controls. The touch sensitive panel 21 registers touch events and passes these signals to a touch screen controller 33, which then processes these signals and sends them to the CPU 30. The CPU 30 includes driver software (stored in memory 31) for telling the CPU 30 how to interpret the touch event information that is sent to the controller 33. The driver software allows the CPU 30 to reconfigure the touch screen controls 23 to represent different sets of control events. For purposes of this disclosure, the touch screen controller 33 and its related driver software will be referred to as the touch screen interface As shown in FIG. 10, the touch sensitive panel 21 (or 21') may be configured to display a specific group of controls, including a zoom in touch control 220, a zoom out touch control 221, a pan up touch control 222, a pan down touch control 223, a pan right touch control 224, a pan left touch control 225 and a save touch control 226 (thereby allowing the user to save the current image). Furthermore, the control buttons 22 may be employed in conjunction with the video control unit 38 to scroll through other control configurations that may be produced by the touch screen interface and displayed on the touch sensitive panel 21 (or 21'). For instance, the touch screen interface may allow the user to initiate transfer of the image to a peripheral device across the output interface, or to retrieve an image from the peripheral device across the output interface.

Figure 11:
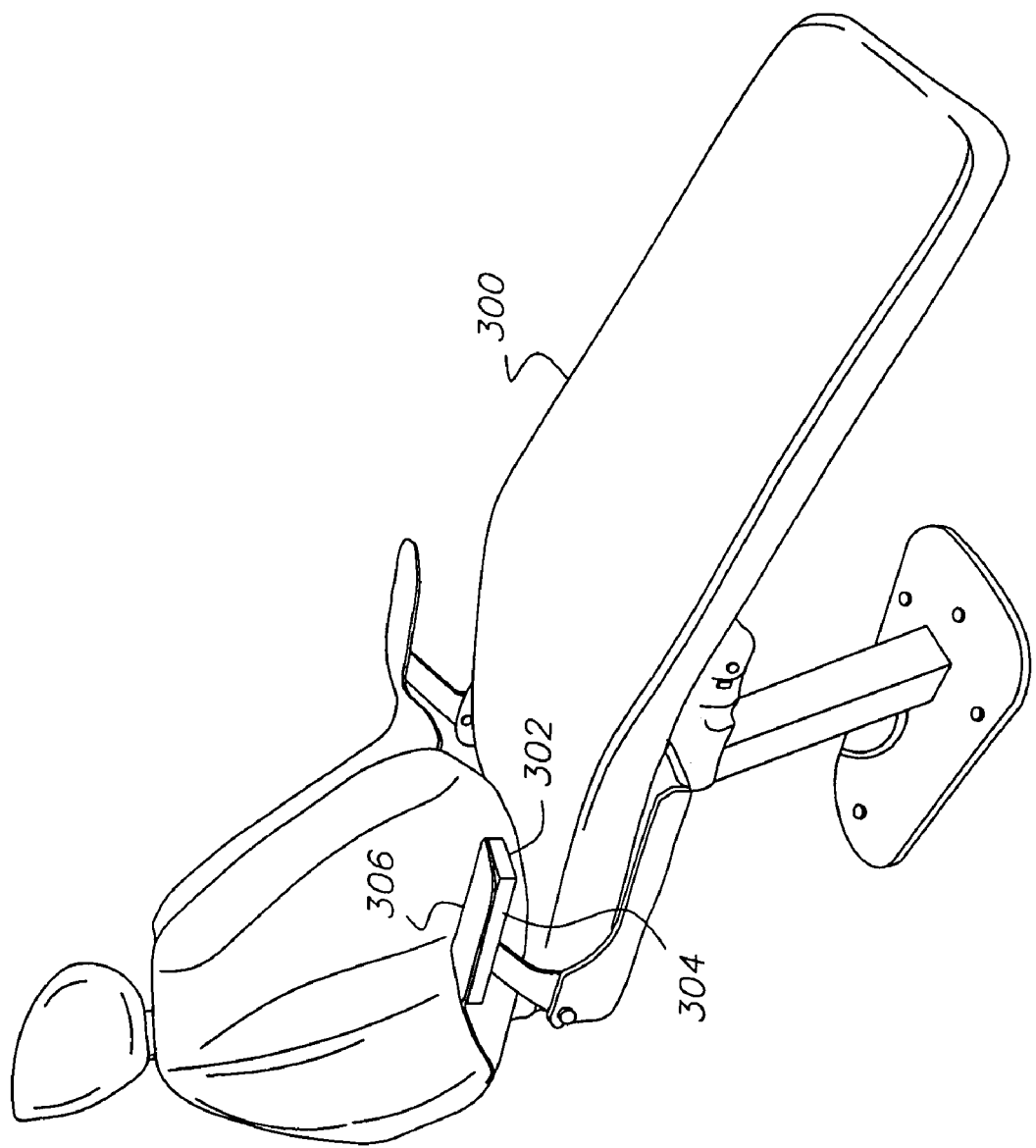
FIG. 11 illustrates a standard dental chair and a portable monitor of the type shown in FIG. 6 that is inserted into a receptacle under one of the armrests on the dental chair.
Figure 12:
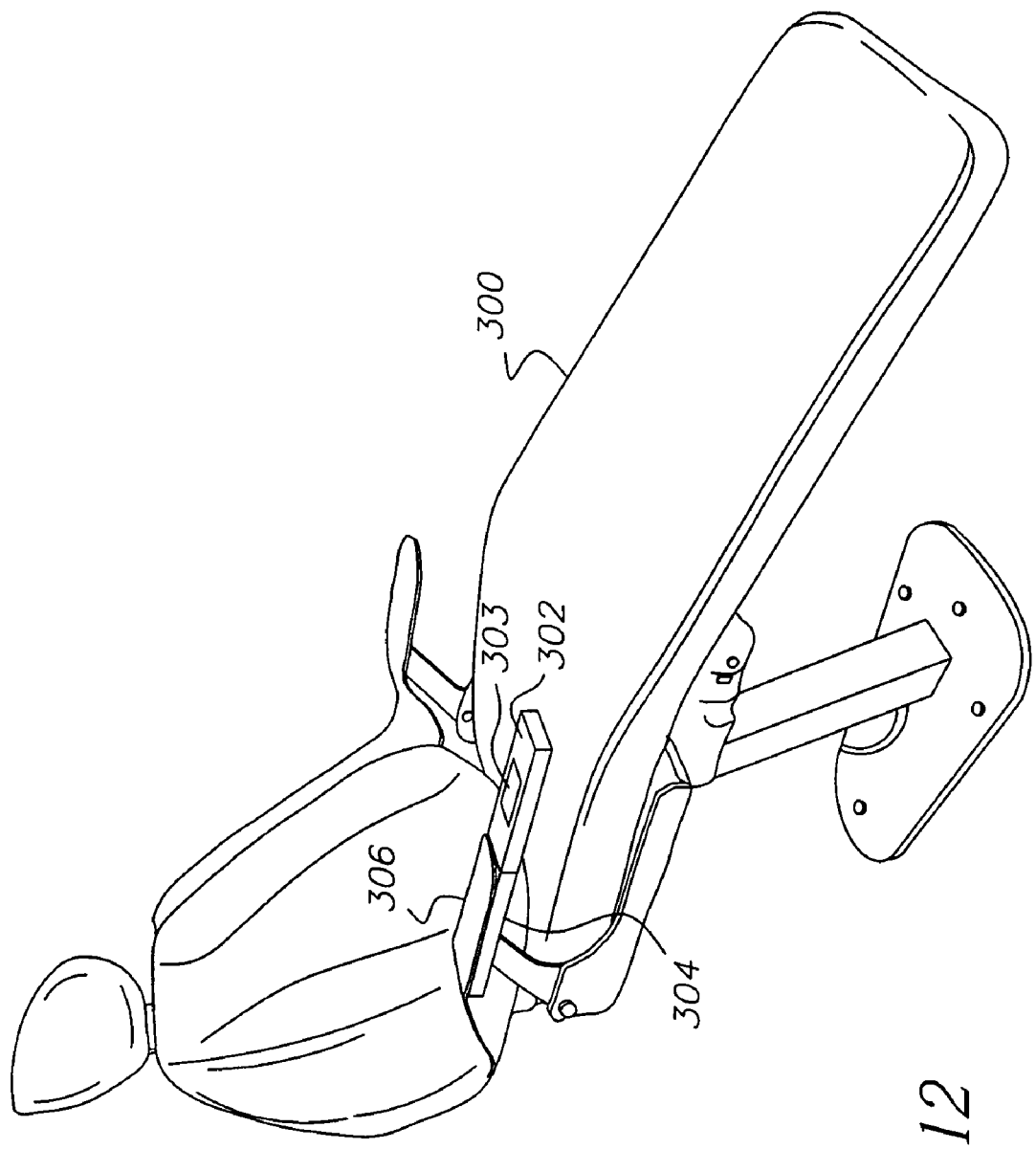
FIG. 12 illustrates how the portable monitor is removed from the receptacle under one of its armrests as shown in FIG. 11.
Figure 13:
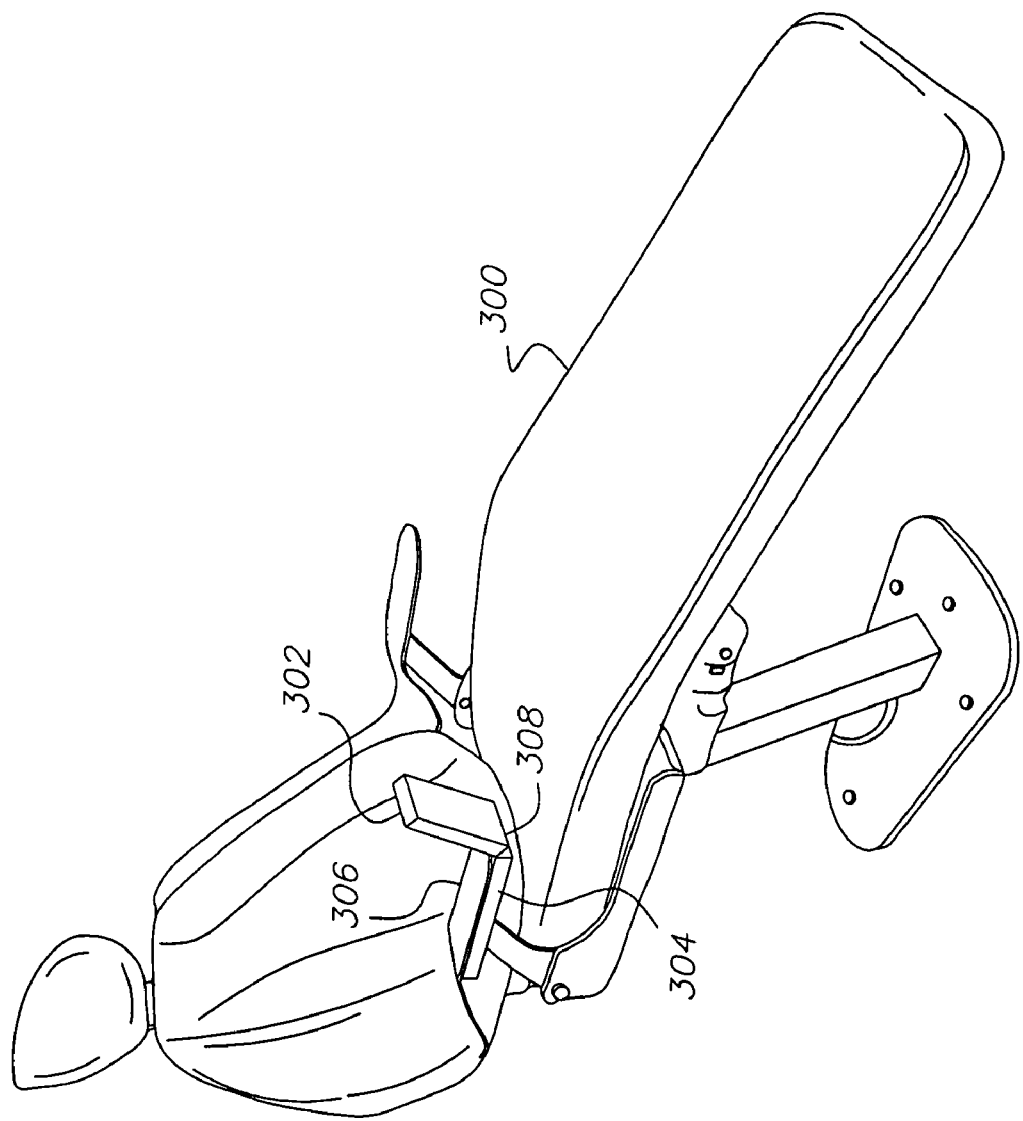
FIG. 13 illustrates how the portable monitor shown in FIG. 12 can be hinged to the receptacle and tilted upward for easy viewing.
Figure 14:
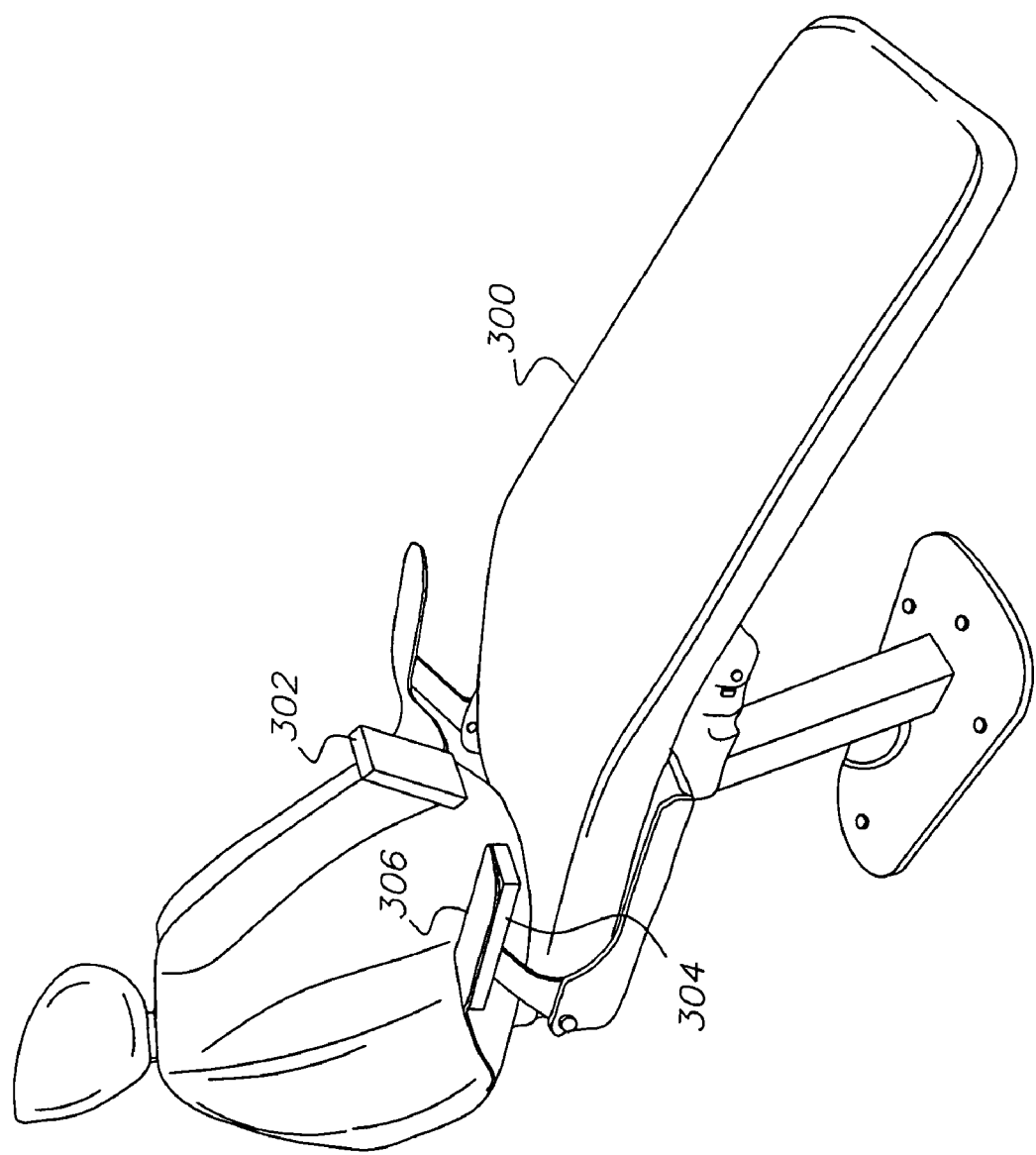
FIG. 14 illustrates how the portable monitor is disconnected from the receptacle shown in FIG. 11 and used as a wireless display.

The specific controls shown in FIG. 10 are intended as a suggestion for a preferred set, but are not intended as a limitation; any number and type of controls may be selected and displayed depending on the application. Moreover, many of the functions needed on a display of this type are dependent on the image being displayed. For instance, different controls may be appropriate depending on whether video or still, or single or multiple, images are being displayed (which are all possible display capabilities of an intra-oral camera). Consequently, typical functions that might be rendered on a touch sensitive panel include:

Zoom (plus and minus)
Pan (left, right, up, down)
Image select
Where to zoom (touching display image itself versus a screen button)
Save image
Add image to patient record
Change exposure
Enhancements
Color modifications
Analyses In a further embodiment of the invention shown in FIGS. 11–14, the handpiece of the intra-oral camera and display system includes electronics and an interface for electrically interconnecting the image signal from the handpiece to the integral base across an electrical linkage, which for example may be a hardwired linkage, an optical linkage, a wireless transmission linkage or any other suitable form of transmission linkage. More specifically, and as shown in connection with FIG. 6, the handpiece 16 would ordinarily include its own light source 120, processor 122, transceiver 124 and power supply 126. The integral base 14, for purposes of this further embodiment, is a small monitor 302 including a small display element 303 (shown best in FIG. 12). More specifically, FIG. 11 illustrates the further embodiment in use with a standard dental chair 300, where a small monitor 302 of the type shown in FIG. 6 is inserted into a receptacle 304 mounted under one of the armrests 306 on the dental chair 300. The receptacle 304 conforms to the shape of the monitor 302 such that the monitor 302 may be withdrawn from the receptacle 304 in order to allow the display element 303 to be seen by the dental practitioner or the patient. For instance, FIG. 12 illustrates how the monitor 302 is removed from the receptacle 304 under one of its armrests 306. As shown in FIG. 13, the monitor 302 shown in FIG. 12 can be hinged to the receptacle 304 via a hinge connection 308 and tilted upward for easy viewing. As was shown in FIG. 6, the integral base 14 may be electrically interconnected with the handpiece via a wireless connection 116. Accordingly, FIG. 14 illustrates how the monitor 302 is disconnected from the its receptacle 304 and used as a small, portable wireless display.

Although preferably mounted under an armrest 306, it should be understood that the receptacle 304 may be mounted to other parts of the dental chair, such as along the leg rest portion or the head rest portion. Indeed, the receptacle may be associated with some other nearby piece of dental apparatus, such as a light fixture. Moreover, the notion of a "receptacle" is merely intended to describe a structural or supporting feature that conforms sufficiently to the monitor 302 so as to support the monitor 302 when it is inserted into the feature and to enable easy withdrawal of the monitor 302 from the feature. Accordingly, this may be without limitation a substantially enclosed space such as a pocket, or a relatively open space such as a framework. The specific material used for the receptacle is unimportant as long as it performs its supporting function, i.e. it may vary from a relatively soft pocket to a firm framework.

Furthermore, the monitor 302 shown in FIGS. 11–14 may include the contamination control devices shown in FIGS. 7A–7D or FIGS. 8A–8C. The touch screen capability shown in FIGS. 9 and 10 may also be incorporated in the monitor 302.

The invention has been described with reference to a preferred embodiment. However, it will be appreciated that variations and modifications can be effected by a person of ordinary skill in the art without departing from the scope of the invention.

PARTS LIST 10 dental camera system
12 portable dental camera
14 integral base
16 handpiece
18 cable
20 display monitor
21 touch sensitive panel
21' limited area
22 user controls
24 removable lens unit
26 lens
28 light emitting apertures
30 CPU
31 CPU memory
32 power supply
33 touch screen controller
34 wireless transceiver
36 flash memory
38 video control unit
40 illuminator control unit
42 illumination source
44 fiber optic
46 electrical conductor
50 image sensor
58 wireless link
60 larger monitor or television receiver
62 printer
64 computer system
66 receptacle
68 RAM card
70 initialize stage
72 illuminate target stage
74 compute stage
76 record stage
78 output compute stage
80 output select stage
100 docking unit
102 recessed area
104 rechargeable batteries
106 charging electrodes
108 battery charger
110 charging electrodes
116 wireless link
118 removable memory card
120 light source
122 processor
124 transceiver
126 power supply
128 rechargeable batteries
130 docking unit
132 battery charger
134 electrodes
136 electrodes
200 pouch
202 flap
204 adhesive
206 slot
208 arrow
210 transparent front panel
212 multiple clear layers
214 tear of tabs
220 zoom in touch control
221 zoom out touch control
222 pan up touch control
223 pan down touch control
224 pan right touch control
225 pan left touch control
226 save touch control
300 standard dental chair
302 small monitor
303 small display element
304 receptacle
306 armrest
308 hinge

What is claimed is:

1. A portable intra-oral capture and display system for use by a dental practitioner in connection with a patient seated in a dental chair, said system comprising:
    a handpiece elongated for insertion into an oral cavity of the patient, said handpiece including a light emitter on a distal end thereof for illuminating an object in the cavity and an image sensor for capturing an image of the object and generating an image signal therefrom;
    a monitor interconnected with the handpiece, said monitor containing electronics for processing the image for display, and a display element for displaying the image, where the interconnection between the monitor and the handpiece includes an electrical connection for communicating the image signal from the image sensor in the camera to the electronics in the monitor;
    a receptacle on the dental chair for receiving the monitor, wherein the receptacle conforms to the monitor such that the monitor may be withdrawn from the receptacle in order to allow the display element to be seen by the dental practitioner or the patient; and
        further including a contamination control device for the portable monitor comprising a pouch enclosing the monitor and having a transparent front panel that is positioned adjacent the display element.

2. The system as claimed in claim 1 wherein the dental chair includes an armrest and the receptacle is mounted underneath the armrest such that the monitor may be withdrawn from the receptacle from under the armrest for easy viewing by the patient or dental practitioner.

3. The system as claimed in claim 1 wherein the monitor is hinged to the receptacle such that the monitor may be withdrawn from the receptacle and tilted upwards for easy viewing by the patient or dental practitioner.

4. The system as claimed in claim 1 wherein the interconnection between the monitor and the handpiece is a wireless connection and the monitor may be completely withdrawn from the receptacle in order to allow the monitor to be handheld by the dental practitioner or the patient.

5. The system as claimed in claim 1 wherein the portable monitor includes a screen for displaying touch screen controls together with the image, and a touch screen interface for providing a plurality of touch screen controls that appear on the screen of the display monitor.

6. A portable display system integrated into a dental chair for use by a dental practitioner in connection with a patient seated in a dental chair, said system comprising:
- a monitor containing electronics for processing an image for display and a display element for displaying the image;
- a receptacle on the dental chair for receiving the monitor, wherein the receptacle conforms to the monitor such that the monitor may be withdrawn from the receptacle in order to allow the display element to be seen by the dental practitioner or the patient; and
- further including a contamination control device for the portable monitor comprising a pouch enclosing the monitor and having a transparent front panel that is positioned adjacent the display element.

7. The system as claimed in claim 6 wherein the dental chair includes an armrest and the receptacle is mounted underneath the armrest such that the monitor may be withdrawn from the receptacle from under the armrest for easy viewing by the patient or dental practitioner.

8. The system as claimed in claim 6 wherein the monitor is hinged to the receptacle such that the monitor may be withdrawn from the receptacle and tilted upwards for easy viewing by the patient or dental practitioner.

9. The system as claimed in claim 6 wherein the portable monitor includes a screen for displaying touch screen controls together with the image, and a touch screen interface for providing a plurality of touch screen controls that appear on the screen of the display monitor.

* * * * *